US00PP07863P

United States Patent [19]

Jessel, Jr.

[11] Patent Number: Plant 7,863

[45] Date of Patent: May 5, 1992

[54] CARNATION PLANT NAMED CFPC CONCERTO

[75] Inventor: Walter H. Jessel, Jr., Salinas, Calif.

[73] Assignee: California Florida Plant Co., L.P., Salinas, Calif.

[21] Appl. No.: 580,258

[22] Filed: Sep. 10, 1990

[51] Int. Cl.[5] ..... A01H 5/00

[52] U.S. Cl. ..... Plt./71

[58] Field of Search ..... Plt./70, 71, 72

[56] References Cited

U.S. PATENT DOCUMENTS

P.P. 5,515 7/1985 Barberet et al. ..... Plt. 77

P.P. 6,369 11/1988 Barberet et al. ..... Plt. 71

*Primary Examiner*—Howard J. Locker

*Attorney, Agent, or Firm*—Christie, Parker & Hale

[57] ABSTRACT

A new and unusual carnation of orchid pink coloration.

1 Drawing Sheet

BACKGROUND OF THE INVENTION

Carnation varieties producing flowers of many different colors are well known. However, it is desirable to provide a new standard variety of carnation producing flowers having orchid pink coloration and other desirable characteristics.

The closest variety to 'CFPC Concerto' is it's parent 'Vanya'. 'CFPC Concerto' differs from Vanya in that the new variety has larger flowers and a vase-life five to six days longer than 'Vanya'. 'CFPC Concerto' also roots more easily than 'Vanya' but has a 7 to 10-day later flowering response.

SUMMARY OF THE INVENTION

The present invention relates to a new and distinct variety of carnation plant which was originated by me in a controlled breeding program by my crossing as seed parent, the variety known as 'Vanya' (varietal denomination 'Londapo') (U.S. Plant Pat. No. 5,515) and as pollen parent, a numbered but unnamed and unpatented seedling of my creation. The varietal denomination of this new carnation is 'CFPC Concerto'.

Among the novel characteristics possessed by the new variety which distinguish it from its parents and all other varieties of which I am aware are flowers of orchid pink flower coloring with a good stem, in a standard, and good flower production. Flowers of the new variety are low in splitting, have good vase-life and are resistant to *botrytis*.

Asexual reproduction by propagation by side shoot cuttings of the new variety as performed in Fremont, Calif., shows that the foregoing and other distinguishing characteristics come true to form and are established and transmitted through succeeding propagations.

BRIEF DESCRIPTION OF THE ILLUSTRATION

The accompanying illustration shows typical specimens of the vegetative growth and flowers of the new variety depicted in color as nearly true as it is reasonably possible to make the same in a color illustration of this character.

DESCRIPTION OF THE NEW VARIETY

The new variety, 'CFPC Concerto', produces large-size, disbud-type flowers which open fully with little bursting of the calyx that causes "splits". The flowers are resistant to *botrytis* and are long lasting after cutting, i.e., have a good vase-life. The new variety has disbud-type flowers which open fully with little bursting of the calyx and splitting. The characteristics heretofore and hereinafter described, make 'CFPC Concerto' especially suitable for commercial cut flower production.

The following is a detailed description of my new variety, with color terminology in accordance with The Royal Horticultural Society Colour Chart (R.H.S.C.C.). The terminology used in the color description herein refers to plate numbers in the aforementioned color chart. Color designations and color descriptions may deviate slightly from the stated values from flowering-to-flowering but the deviations will be within the range expected from varying environmental, seasonal and cultural conditions.

The information provided herein is based on observations of plants grown inside commercial greenhouses at Fremont, and Salinas, Calif. The height of plant and flower and foliage size are established as an average using standard commercial cultural practices.

Name: 'CFPC Concerto'.

Classification:

*Botanical.*—*Dianthus caryophyllus.*

*Commercial.*—Carnation, standard disbud type.

Parentage:

*Female parent.*—'Vanya'

*Male parent.*—Unnamed seedling (No. 00167).

Plant:

*Height.*—About 48 to 49½ inches.

*Growing habit.*—Herbaceous, upright.

*Blooming habit.*—Terminal as a disbud.

*Blooming season.*—Year round.

*Rooting time.*—17-20 days.

*Stem.*—Excellent breaking action.

*Mutation prone.*—No.

*Disease resistance.*—Unknown, but no *botrytis* sensitivity.

*Temperature tolerance.*—Typical for carnation.

Foliage:

*Color.*—Upper side: Near to 189A. Lower side: Near to 191A.

*Size.*—About 6½ inches long and about ½ inch wide at base of plant.

*Quantity.*—Numerous.

*Shape.*—Lanceolate.

*Texture.*—Smooth.

*Ribs.*—Central keel.

*Arrangement.*—Bi-lateral along stem.

*Stem.*—Color — green.

Bud:

*Shape.*—Oval.

*Color.*—Near to 143B.

*Length.*—About $1\frac{5}{8}$ inches.

*Diameter.*—About $\frac{1}{2}$ inch.

Calyx:

*Number of lobes.*—About 5.

*Length.*—About $1\frac{5}{8}$ inches.

*Width.*—About $\frac{1}{2}$ to $\frac{5}{8}$ inch.

*Color.*—Outside — near to 143B. Inside — near to 140D.

Bloom:

*Size.*—Diameter average: About $3\frac{1}{4}$ to $4\frac{1}{4}$ inches.

*Depth average: About* $1\frac{1}{2}$ to 2 inches.

*Borne.*—Terminal as disbudded.

*Color.*—General tonality: Orchid pink. Upper side: Near to from 73A to 73B. Lower side: Near to 65A. Center: Near to 73A. Outer petals: Near to 73A.

*Keeping habit.*—10 to 14 days.

*Fragrance.*—Little.

Petals:

*Outer petals.*—Length: About $2\frac{1}{4}$ inches. Width: About $1\frac{3}{8}$ inches.

*Texture.*—Smooth.

*Form.*—Fan shaped, serrated edge.

*Number.*—About 53.

*Appearance.*—Shiny.

Reproductive organs Not visible in this variety.

*Stamens.*—Number: About 7 to 9. Arrangement: Around the ovary.

*Anthers.*—Number: About 7 to 9. Length: About $\frac{1}{8}$ inch. Color: Near to 161C.

*Filaments.*—Length: About 1 inch. Color: Near to 161D.

*Pistils.*—Length: About $1\frac{1}{2}$ inches. Number: About 2. Color: Style — near to 36D (White at maturity).

*Stigma.*—Number: About 2. Color: White.

*Fertility.*—Male: Sterile. Female: Extremely poor.

*Ovary.*—Shape: Conical, ribbed. Color: Base — greenish white. Body — greenish yellow. Apex — tan.

I claim:

1. A new and distinct variety of carnation plant, substantially as shown and described, characterized particularly by flowers of attractive pink coloration.

* * * * *

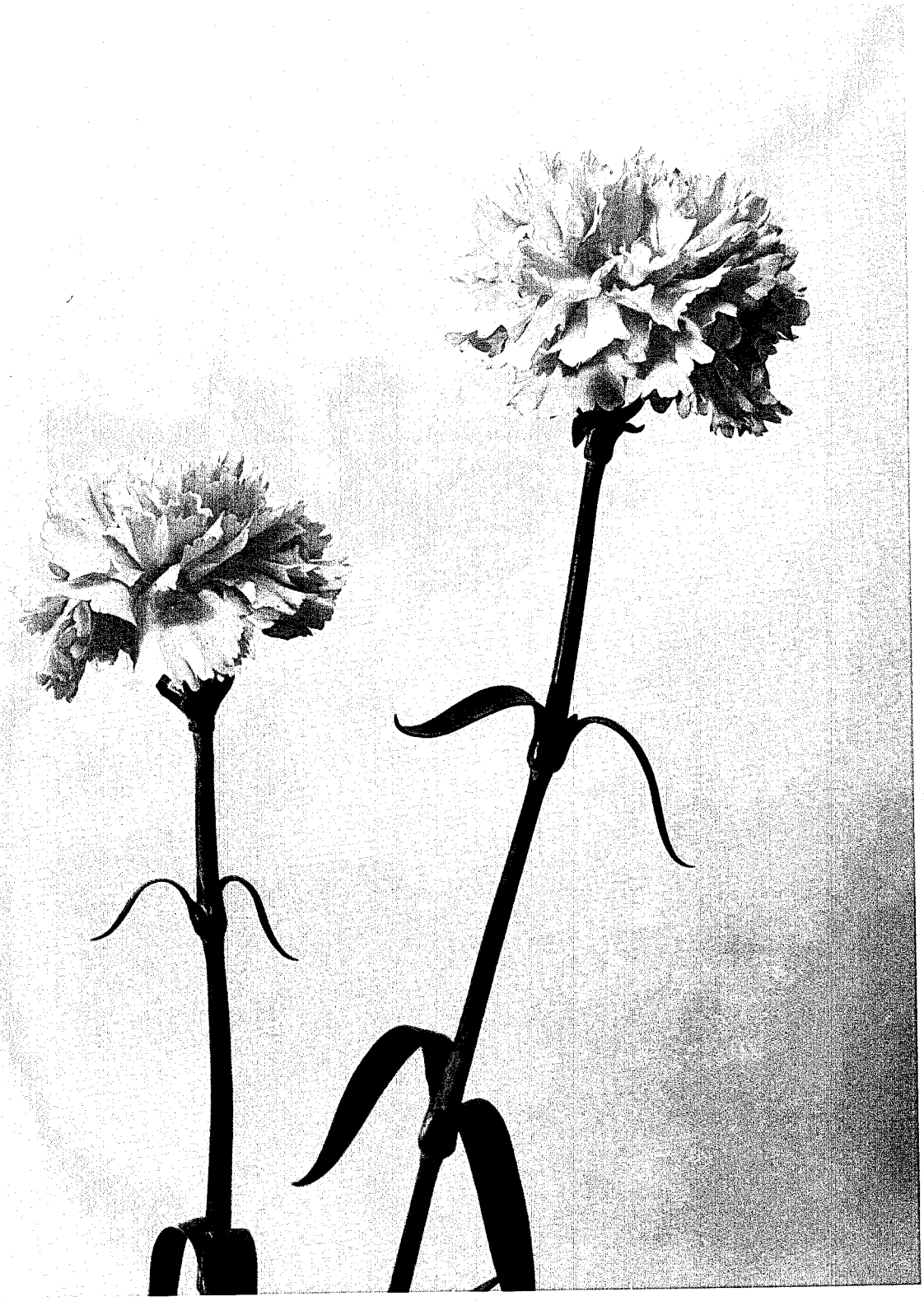

UNITED STATES PATENT AND TRADEMARK OFFICE

CERTIFICATE OF CORRECTION

PATENT NO. : Plant 7,863

DATED : May 5, 1992

INVENTOR(S) : Walter H. Jessel, Jr.

It is certified that error appears in the above-identified patent and that said Letters Patent is hereby corrected as shown below:

Column 3, line 7, change "1-5/8" to -- 1-1/3 --.

Column 3, line 11, change "1-5/8" to -- 1-1/3 --.

Column 4, line 7, move "Not visible in this variety." to the next line.

Signed and Sealed this

Thirty-first Day of August, 1993

Bruce Lehman

*Attest:*

BRUCE LEHMAN

*Attesting Officer*

*Commissioner of Patents and Trademarks*